United States Patent
Reisner (12)

(10) Patent No.: US 6,451,355 B1
(45) Date of Patent: Sep. 17, 2002

(54) COMPOSITION TO TREAT DIABETES

(76) Inventor: Howard M. Reisner, 2329 Murray Ave., Pittsburgh, PA (US) 15217

( * ) Notice: Subject to any disclaimer, the term of this patent is extended or adjusted under 35 U.S.C. 154(b) by 0 days.

(21) Appl. No.: 09/906,379

(22) Filed: Jul. 16, 2001

Related U.S. Application Data

(60) Provisional application No. 60/218,601, filed on Jul. 17, 2000.

(51) Int. Cl.7 .......................... A01N 68/00; A61K 35/78; A61K 35/413
(52) U.S. Cl. ........................................ 424/725; 424/528
(58) Field of Search .................................. 424/725, 768, 424/528; 514/169, 182; 536/123

(56) References Cited

U.S. PATENT DOCUMENTS 5,847,109 A * 12/1998 Garti et al. ................. 535/123
6,060,465 A * 5/2000 Miljkovic et al. .......... 514/169

OTHER PUBLICATIONS

Sharma et al.: Effect of Fenugreek Seed on Blood Glucose and Serum Lipids in Type 1 Diabetes; 1990, Euro. J. of Clinical Nutri., vol. 44, pp. 301–306.*

* cited by examiner

Primary Examiner—Jon P. Weber
Assistant Examiner—Patricia Patten
(74) Attorney, Agent, or Firm—Webb Ziesenheim Logsdon Orkin & Hanson, P.C.

(57) ABSTRACT

A composition for treating diabetes is disclosed. The composition includes fenugreek and bile from the gallbladder of ruminant mammals. The composition is used to treat diabetes through regular periodic dose administration.

18 Claims, No Drawings

COMPOSITION TO TREAT DIABETES

CROSS-REFERENCE TO RELATED APPLICATION

This application claims priority from U.S. Provisional Patent Application Ser. No. 60/218,601, filed Jul. 17, 2000, and entitled "Composition to Treat Diabetes."

BACKGROUND OF THE INVENTION

1. Field of the Invention

The present invention is generally directed to compositions and methods for treating diabetes mellitus.

2. Description of the Prior Art

Diabetes mellitus is a disorder of carbohydrate metabolism resulting from insufficient production of or reduced sensitivity to insulin. In persons who have diabetes, the normal ability of body cells to use glucose is inhibited, thereby increasing blood sugar levels. As more glucose accumulates in the blood, excess levels of sugar are excreted in the urine. Corresponding symptoms of diabetes include increased urinary volume and frequency, thirst, itching, hunger, weight loss, and weakness.

There are three variations of diabetes. Type I is insulin-dependent diabetes mellitus for which insulin injection is required. In this type, insulin is not secreted by the pancreas and must be taken by injection. Type II, non-insulin-dependent diabetes mellitus may be controlled by dietary restriction. It derives from sluggish pancreatic secreted insulin. Type III diabetes is caused by the body rejecting the insulin secreted by the pancreas.

Treatment aimed at controlling diabetes involves placing patients on restrictive diets designed to help them reach and maintain normal body weight and to limit their intake of carbohydrates and fats. Diabetics who are unable to produce insulin in their bodies receive regular injections of insulin. Insulin derived from the pancreatic extract of pigs, sheep, and oxen has been used for many years for this purpose. More recently, recombinant DNA technology has made synthetic human insulin available.

Complications from diabetes typically involve the cardiovascular system which accounts for the majority of diabetes-related deaths. Other serious complications include a condition known as diabetic retinopathy (retinal changes leading to blindness), kidney disease, and frequent infection.

Medications have also been employed to help maintain blood glucose levels within target ranges. These medications improve the body's ability to use insulin and decrease the production of glucose by the liver. An example of this type of medication is troglitazone, which is supplied under the name Rezulin® by Parke-Davis. However, troglitazone has been taken off the market by the USFDA because of reported liver injury caused by its use. Other medications often cause nausea when used.

There remains a need for a treatment that will improve the body's ability to use insulin and decrease the production of glucose released by the liver without adverse health effects.

SUMMARY OF THE INVENTION

The present invention is directed to a composition for treating diabetes. The composition includes an effective amount of fenugreek and an effective amount of bile from the gallbladder of a ruminant. The bile and fenugreek powder is mixed together to form a paste from which pills are formed.

The present invention is also directed to a method for treating diabetes. The method involves administering periodic doses of a composition including an effective amount of fenugreek and an effective amount of bile from the gallbladder of a ruminant. The treatment method of the present invention minimizes the complications from diabetes and helps to reverse many of its chronic side effects.

These and other advantages of the present invention will be clarified in the description of the preferred embodiment taken together with the attached drawings in which like reference numerals represent like elements throughout.

DETAILED DESCRIPTION OF THE PREFERRED EMBODIMENT

The composition for treating diabetes of the present invention includes fenugreek and bile from the gallbladder of ruminants, such as cattle, sheep, bison, and goats. Bile from the gallbladder of cattle is preferred. The fenugreek is preferably pulverized into a powder. The bile and fenugreek is mixed together to form an acceptable medium for administering a dose. This acceptable medium can be a solution, a syrup, an emulsion, a dispersion, a paste, or a pill. It is preferred that a small amount of water be added to the mixture of fenugreek and bile to aid in the formation of pills. Pills are the preferred medium for administering the dose.

Alternatively, the active components of fenugreek can be made synthetically and be formulated into the composition of the present invention. Fenugreek, also spelled foenugreek, is a slender annual herb of the pea family. Its dried seeds have been used for generations as a food, a flavoring, and a medicine. Steroidal saponins account for many of the beneficial effects of fenugreek, particularly the inhibition of cholesterol absorption and synthesis. The seeds are rich in dietary fiber, which may be the reason it can lower blood sugar levels in diabetics.

It is contemplated, as part of the present invention, that fennel seed can be used to replace all or part of the fenugreek in the composition for treating diabetes of the present invention. Fennel seed, like fenugreek, is an herb native to southern Europe and the Mediterranean area.

The second primary component of the present invention is bile from the gallbladder of ruminant mammals. Synthetic compositions of the active components in bile can also be used in the composition of the present invention. Bile, also called gall, is a for concentration, storage, or transport into the first region of the small intestine, the duodenum. Bile is composed of bile acids and salts, cholesterol, pigments, water, and electrolyte chemicals that keep the total solution slightly acidic. The pH of bile is typically about 5 to 6. Bile acid typically includes cholic, deoxycholic, chenodeoxycholic, and lithocholic acids. The bile salts include the salts of these acids with amino acids, such as glycine and taurine. Other components of bile include hemoglobin, mucus, serum proteins, lecithin, neutral fats, fatty acids, and urea.

The method of treating diabetes of the present invention begins with the preparation of doses of a composition for treating diabetes which includes an effective amount of fenugreek and/or fennel seed mixed together with an effective amount of bile from the gallbladder of ruminant mammals. The doses are often mixed together in a paste to form pills. The doses are administered at regular intervals throughout the day. By administered, what is meant is providing the composition to a patient and the patient consuming the composition by accepted medical practice. Accepted medical practice is meant to include any method approved by the American Medical Association for introduction of the composition into the human body.

The amount of the composition administered as part of the doses is an amount sufficient to counteract the effects of diabetes. These effects or symptoms which are affected will include blood glucose levels, stomach neuropathy, appetite, sleep habits, general energy level, strength, body weight, reflux, headaches, Minear's disease, and eye sight. A sufficient amount is an amount, when administered, that provides relief from one or more of the effects or symptoms.

When the composition is administered in the form of a pill, it is preferred that the pills be used with approximate dimensions of 0.5 inches diameter and 0.125 inches thickness. The preferred dose administration is three pills administered three times during the day.

EXAMPLE

A composition for treating diabetes was made by mixing approximately 3 ounces by weight of pulverized fenugreek and approximately 1 ounce by weight of bile from the gallbladder of a calf. A small amount of water was added to the mixture to form a paste from which pills were formed. Each pill weighed approximately that of an average 5 gram aspirin pill.

The pills were administered to a male subject aged 58 who suffers from Type III diabetes and demonstrated particular side effects, such as irregularity, stomach neuropathy, poor appetite, insomnia, lethargy, reflux, migraine headaches, Minear's disease, and deteriorating eyesight. The subject took three pills, three times during the day and just prior to going to sleep for the night. The subject reported a marked improvement in all of the above-mentioned symptoms after one week to two weeks of treatment.

The invention has been described with reference to the preferred embodiment. Obvious modifications and alterations will occur to others upon reading and understanding the preceding detailed description. It is intended that the invention be construed as including all such modifications and alterations insofar as they come within the scope of the appended claims or the equivalents thereof.

I claim:

1. A composition for treating diabetes to be taken in oral doses comprising an effective amount of a pulverized seed from an herb selected from fenugreek and fennel and an effective amount of bile from the gallbladder of a ruminant mammal.

2. The composition of claim 1, wherein the ruminant mammal is selected from one or more of the group consisting of a domesticated bovine animal, sheep, bison, and goat.

3. The composition of claim 1, wherein the composition is in a form selected from the group consisting of a suspension, a paste, and a pill.

4. The composition of claim 1, further comprising water.

5. The composition of claim 1, wherein the herb seed is fenugreek seed.

6. The composition of claim 1 wherein the bile comprises bile acids and their corresponding salts, cholesterol, cholic acid and its salts, deoxycholic acid and its salts, chenodeoxycholic and its salts, lithocholic acid and its salts, serum proteins, lecithin, neutral fats, fatty acids, and urea.

7. The composition of claim 6, wherein the salts are salts of amino acids.

8. The composition of claim 7, wherein the amino acids are selected from the group consisting of glycine and taurine.

9. A method for treating diabetes, wherein periodic oral doses of a composition comprising an effective amount of a pulverized seed from an herb selected from fenugreek and fennel, and an effective amount of bile from the gallbladder of a ruminant mammal are administered to a diabetic.

10. The method of claim 9, wherein the ruminant mammal is selected from one or more of the group consisting of a domesticated bovine animal, sheep, bison, and goat.

11. The method of claim 9, wherein the composition is in a form selected from the group consisting of a suspension, a paste, and a pill.

12. The method of claim 9, wherein the composition further comprises water.

13. The method of claim 9, wherein the herb seed is fenugreek seed.

14. The method of claim 9, wherein, the bile component comprises bile acids and their corresponding salts, cholesterol, cholic acid and its salts, deoxycholic acid and its salts, chenodeoxycholic and its salts, lithocholic acid and its salts, serum proteins, lecithin, neutral fats, fatty acids, and urea.

15. The method of claim 9, wherein the doses are administered at regular intervals throughout the day.

16. The method of claim 15, wherein the dose of the composition is an amount sufficient to counteract the effects of diabetes.

17. The method of claim 9, wherein the dose is in the form of a pill with dimensions of about 0.5 inches diameter and about 0.125 inches thickness.

18. The method of claim 17, wherein the dose administered is three pills administered three times during the day.

* * * * *

UNITED STATES PATENT AND TRADEMARK OFFICE
CERTIFICATE OF CORRECTION

PATENT NO.   : 6,451,355 B1                                          Page 1 of 1
DATED        : September 17, 2002
INVENTOR(S)  : Howard M. Reisner It is certified that error appears in the above-identified patent and that said Letters Patent is hereby corrected as shown below:

Column 2,
Line 46, "is for concentration" should read -- is a greenish yellow secretion that is produced in the animals' liver and passed to the gallbladder for concentration --.

Signed and Sealed this

Eighteenth Day of February, 2003

JAMES E. ROGAN
*Director of the United States Patent and Trademark Office*